(12) United States Patent
Malinowski

(10) Patent No.: US 7,337,003 B2
(45) Date of Patent: Feb. 26, 2008

(54) IMPLANTABLE PULSE GENERATOR CASE

(75) Inventor: Zdzislaw B. Malinowski, Castaic, CA (US)

(73) Assignee: Advanced Bionics Corporation, Valencia, CA (US)

( * ) Notice: Subject to any disclaimer, the term of this patent is extended or adjusted under 35 U.S.C. 154(b) by 489 days.

(21) Appl. No.: 11/043,651

(22) Filed: Jan. 25, 2005

(65) Prior Publication Data

US 2006/0167534 A1  Jul. 27, 2006

(51) Int. Cl.
*A61N 1/375* (2006.01)
(52) U.S. Cl. .............................. 607/36; 607/37; 607/38
(58) Field of Classification Search .................. 607/36, 607/37, 38
See application file for complete search history.

(56) References Cited

U.S. PATENT DOCUMENTS

| | | |
|---|---|---|
| 4,180,078 A | 12/1979 | Anderson |
| 4,411,276 A | 10/1983 | Dickhudt et al. |
| 4,603,696 A | 8/1986 | Cross, Jr. et al. |
| 4,712,557 A | 12/1987 | Harris |
| 5,103,818 A * | 4/1992 | Maston et al. .................. 607/9 |
| 5,370,669 A * | 12/1994 | Daglow et al. ............... 607/36 |
| 5,730,628 A | 3/1998 | Hawkins |
| 5,782,891 A * | 7/1998 | Hassler et al. ................ 607/36 |
| 5,861,042 A * | 1/1999 | Buechel et al. ............. 128/898 |
| 6,006,135 A * | 12/1999 | Kast et al. ..................... 607/37 |
| 6,321,126 B1 * | 11/2001 | Kuzma ........................ 607/137 |

* cited by examiner

*Primary Examiner*—George R. Evanisko
*Assistant Examiner*—Joseph Stoklosa
(74) *Attorney, Agent, or Firm*—Travis K. Laird; AdvantEdge Law Group, LLC

(57) ABSTRACT

An implantable medical device, e.g., a stimulator, having a sealed housing and method of making the same. An exemplary embodiment of the device includes a case frame defining a cavity, the cavity extending at least substantially through the case frame, which cavity may contain electronics or a power source, and at least one lid configured to be sealingly coupled to the case frame. A feedthru opening may also be included in the case frame.

19 Claims, 13 Drawing Sheets

IMPLANTABLE PULSE GENERATOR CASE

BACKGROUND

Implantable pulse generator systems and other stimulation devices are used to treat chronic pain by providing electrical stimulation pulses from an electrode array placed epidurally near a patient's spine. Spinal cord stimulation (SCS) is a well accepted clinical method for reducing pain in certain populations of patients. SCS systems typically include an implantable pulse generator (IPG), lead wires and/or lead extensions, and electrodes connected to the lead wires.

The pulse generator generates electrical pulses that are delivered to the dorsal column fibers within the spinal cord through the electrodes which are implanted along the dura of the spinal cord. In a typical situation, the attached lead wires exit the spinal cord and are tunneled around the torso of the patient to a sub-cutaneous pocket where the pulse generator is implanted.

In order to protect the electronic circuitry from environmental conditions and/or other damage while the IPG is implanted within a patient, the IPG is frequently enclosed in a titanium case to provide protection and a hermetic, or completely sealed, environment. For example, the titanium case frequently includes two halves. Recesses are formed in each of the halves such that when the two halves are coupled together, holes are defined therein. Feedthrus extend through these holes to allow the lead wires or lead extensions to be electrically coupled to the electronic circuitry of the IPG. In some circumstances, it may be difficult to ensure that the assembly is hermetically sealed.

In particular, to properly establish the feedthrus, the titanium halves often must be aligned with respect to each other and with respect to the feedthru member. The assembly is then welded. The welded assembly is subsequently checked for leaks. If the resulting assembly is not hermetically sealed, the assembly is then reworked. Even if the assembly is sealed during formation, it may be possible for the feedthrus to later develop leaks. If the feedthrus do leak, resulting in the ingress of moisture, the IPG may fail prematurely, such as by damaging the electronic circuit of the IPG.

Moreover, the traditionally used titanium halves are difficult to properly weld such that a hermetically sealed case is produced. The traditionally shaped case is welded along a number of edges having varying profiles. Consequently, it is difficult to establish a constant welding speed and the work piece is rotated for proper weld orientation, often resulting in poor weld penetration. Additionally, because traditional cases butted mating pieces together and due to poor tolerances from manufacturing methods, little or no material was present under the welded seam, resulting in inferior welds.

Further, some designs allow the battery to be recharged using an external power source. The use of a highly conductive case may limit the rate with which the battery in an implanted medical device may be charged inductively through the skin. For example, commercially pure titanium, while relatively easy to machine, may be subject to induced heating of the case as a result of eddy currents caused during inductive charging.

SUMMARY

An embodiment of an implantable pulse generator case may include a case frame having a cavity defined therein, the cavity extending through the case frame and being configured to have pulse generating electronics and a power source at least partially contained therein. Additionally, the exemplary case may include side lids configured to be sealingly coupled, such as by laser welding, to the case frame and a connector block cover coupled to the case frame.

BRIEF DESCRIPTION OF THE DRAWINGS

The accompanying drawings illustrate various embodiments of the present apparatus and method and are a part of the specification. The illustrated embodiments are merely examples of the present apparatus and method and do not limit the scope of the disclosure.

Throughout the drawings, identical reference numbers designate similar, but not necessarily identical, elements.

DETAILED DESCRIPTION

A case assembly is provided herein that may be used to hermetically seal an implantable pulse generator. The case assembly generally includes a case frame with a cavity defined therein that extends between opposing sides. The cavity is configured to have an electronic circuit board or hybrid and a power source hermetically contained therein. The electronic circuit board or hybrid may include receiving, processing, and transmitting and other circuitry coupled to a printed circuit board. The exemplary case assembly also includes side lids configured to be coupled to the case frame to thereby seal each of the opposing sides. The case assembly also includes a feedthru member that is laser welded or otherwise hermetically coupled to the case to ensure hermeticity. The feedthru member provides electrical coupling between the electronic circuit board contained in the hermetically sealed case and external connectors, leads, and lead extensions, which are directed to a desired location in the patient.

The present case configuration provides for the rapid and reliable formation of an implantable pulse generator. Specifically, the case frame can be precisely machined on any number of machine tool centers. Additionally, the side lids and feedthru opening can be made with high tolerances permitting the case assembly process to be both simple and consistent.

In the following description, for purposes of explanation, numerous specific details are set forth in order to provide a thorough understanding of the present method and apparatus. It will be apparent, however, to one skilled in the art, that the present method and apparatus may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
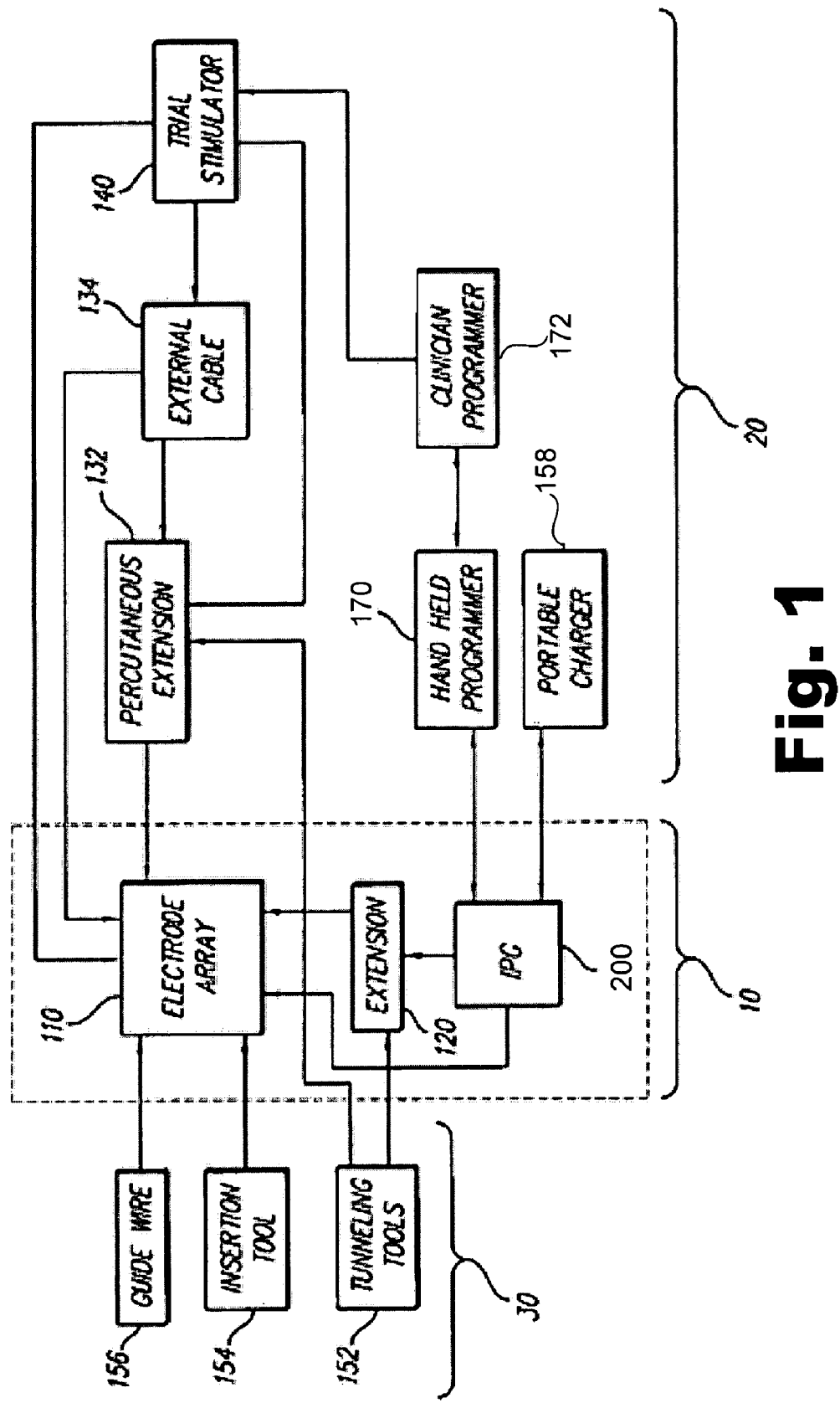
FIG. 1 illustrates a schematic view of a spinal cord stimulation system, according to one exemplary embodiment.

Referring now to the Figures, FIG. 1 illustrates a schematic view of a spinal cord stimulation system according to one exemplary embodiment. FIG. 1 is a block diagram illustrating several exemplary components that may be used in one exemplary spinal cord stimulation (SCS) system. These components may be subdivided into three broad categories: implantable components (10), external components (20), and surgical components (30). While the present exemplary embodiment is described in the context of a spinal cord stimulation system, the present method and apparatus may similarly be incorporated with any number of stimulation systems, as will be understood by one of ordinary skill in the art.

As seen in FIG. 1, the implantable components (10) of the exemplary SCS include an implantable pulse generator (IPG) (200), an electrode array (110), and a lead or lead extension (120). As will be discussed in more detail below, the implantable pulse generator (200) is hermetically sealed and has a case assembly that includes a case frame, side lids, and a connector block cover. Such a configuration may improve the reliability and repeatability of processes for forming an IPG.

The lead or lead extension (120) is used to electrically couple the electrode array (110) to the IPG (200). In an exemplary embodiment, the IPG (200), described more fully below, includes a rechargeable, multi-channel, sixteen-contact, telemetry-controlled, pulse generator. A tool-less lead connector is also part of the IPG (200). The lead connector allows the electrode array (110), a lead, or a lead extension (120) to be detachably secured, or electrically connected, to the IPG (200). This lead connector may be of the type described in a commonly assigned U.S. patent application entitled "Connector for Use in An Implantable Stimulator Device," which is filed concurrently herewith and is hereby incorporated by reference. Any other suitable lead connector may also be used.

The electrode array (110) and its associated lead system typically interface with the implantable pulse generator (200) via a lead extension system (120). As needed, for testing and/or fitting purposes, the electrode array (110) may also interface with an external trial stimulator (ETS) (140) through one or more percutaneous lead extensions (132), connected to the trial stimulator (140) through an external cable (134). In this manner, the individual electrode contacts included within the electrode array (110) may receive an electrical stimulus from either the trial stimulator (140) or the IPG (200), but not at the same time.

As suggested in the block diagram of FIG. 1, the lead and/or lead extension(s) (120), as well as the percutaneous extension(s) (132) are inserted through the patient's tissue through the use of appropriate surgical tools (ST) (30). In particular, the lead and/or lead extension(s) (120) and the percutaneous extension(s) (132) may be inserted through the use of tunneling tools (152), as are known in the art, or as are especially developed for purposes of spinal cord stimulation systems. In a similar manner, the electrode array (110) may be implanted in its desired position adjacent to the spinal column of the patient through the use of an insertion needle (154) and a guide wire (156). The insertion needle, according to one exemplary embodiment, may be a 15-gauge Touhy needle.

Additionally, a lead blank may be used to aid in the insertion process. A lead blank is a somewhat flexible wire that approximates the lead diameter of the lead that is to eventually be implanted. A clinician uses the lead blank to clear the path through the insertion needle and into the epidural space before inserting the epidural electrode array. Use of the lead blank prevents damage to the electrode array when tissue is obstructing its insertion path.

Typically, the IPG (200) is placed in a surgically-made pocket either in the abdomen or just at the top of the buttocks. The IPG (200) may, of course, also be implanted in other locations of a patient's body. It is noted that while the exemplary IPG (200) shown includes a rechargeable battery as its power source, and while such a rechargeable power source is described herein, any power source may be used with the IPG (200), including non-rechargeable power sources, such as an implantable battery of the type commonly used in implantable pacemakers.

Once implanted, the IPG (200) is connected to a lead system. One exemplary lead system includes a lead, the lead extension (120), if desired, and the electrode array (110). The lead extension (120), for example, may be tunneled up to the spinal column. Once implanted, the electrode array (110) and lead extension (120) are intended to be permanent. In contrast, the IPG (200) may be replaced when its power source fails or is no longer rechargeable.

According to one exemplary embodiment, the IPG (200) provides electrical stimulation through a plurality of terminal electrode contacts. For example, electrical stimulation may be provided through conductors or conductor wires that are coupled to the electrode array (110). A common type of electrode array (110), for example, is incorporated in an "in-line" lead. An in-line lead includes individual electrode contacts spread longitudinally along a small-diameter, flexible, insulative carrier. The flexible carrier has small conductor wires embedded (or otherwise carried) therein for electrically contacting each of the individual electrode contacts.

An external handheld programmer (170) and/or portable charger (158) may also be inductively coupled to the implanted IPG (200) to provide programming and to recharge the power source of the portable charger. A clinical programmer (172) is able to externally access the hand-held programmer (170) to control the operation of the IPG (200). Accordingly, the IPG (200) has a hermetically sealed case assembly that may subsequently be implanted within a patient's body. An exemplary IPG (200) and its associated case assembly will be discussed in further detail below.

Figure 2:
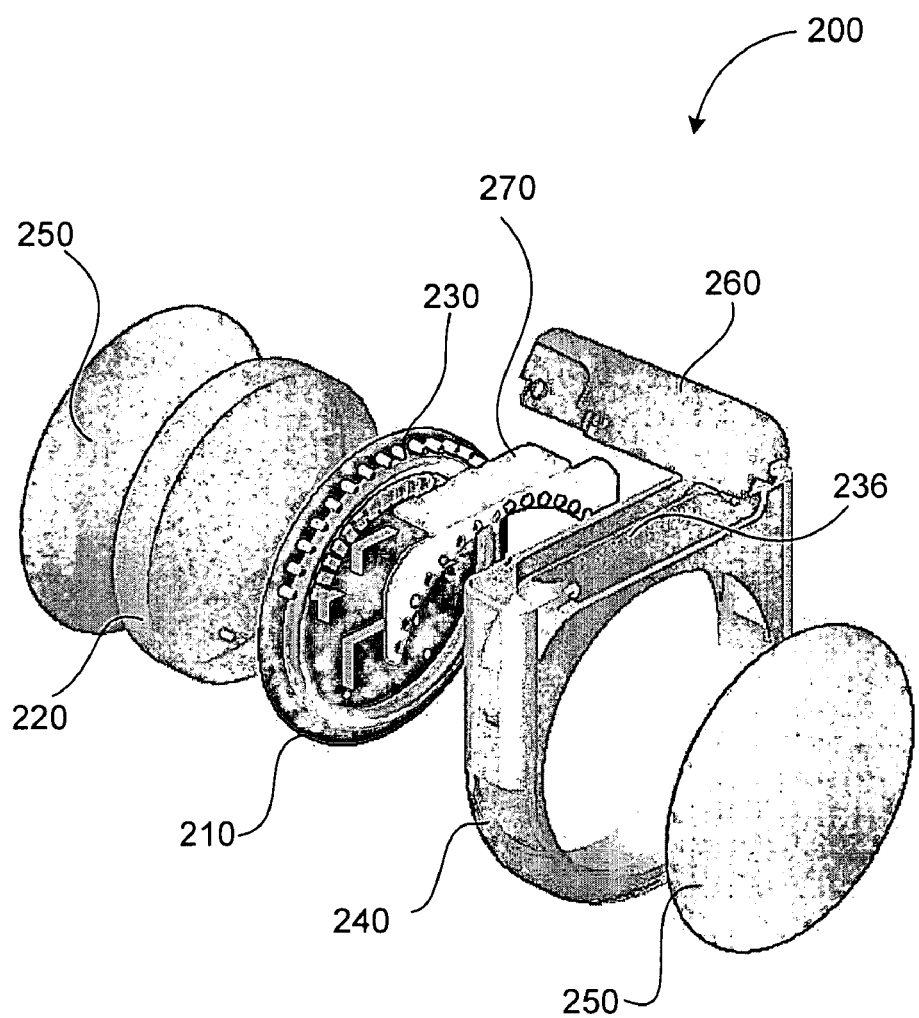
FIG. 2 illustrates a perspective exploded view of an implantable pulse generator, according to one exemplary embodiment.
Figure 10:
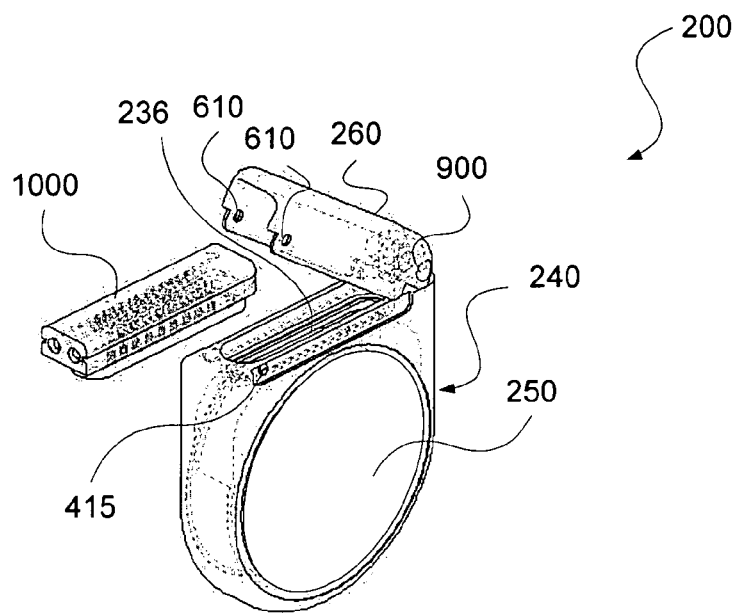
FIG. 10 is a perspective view of a lead connector block being inserted into an assembled stimulator device, according to one exemplary embodiment.

FIG. 2 illustrates an exploded perspective view of an exemplary stimulator device also commonly referred to in the medical device industry as an "IPG" (200). As illustrated in FIG. 2, the stimulator device (200), also referred to herein as an IPG, includes an electronic circuit board or hybrid (210), which includes several components, a power source (220), and hybrid pins (230) inserted into the circuit board. The electronic circuit board or hybrid (210) includes electronic circuitry thereon that selectively couples to the power source (220) to the feedthru member (236). More specifically, the pins (230) inserted into the circuit board (210) electrically couple the electronic circuit board or hybrid (210) thru the flexible or "flex" connector (270) to a feedthru member (236). The feedthru member (236) is coupled to a lead connector block (1000; FIG. 10) that in turn is configured to be coupled to leads that are directed from the exemplary stimulator device (200) to the desired location.

According to the exemplary embodiment illustrated in FIG. 2, the electronic circuit board or hybrid (210), which includes several components, and pins (230) inserted into the circuit board is formed by electrically coupling the electronic components to the printed circuit board. According to one exemplary method, the components of the electronic circuit board or hybrid (210) are physically coupled to the circuit board using solder or conductive epoxy. These components may include, but are in no way limited to, a microcontroller coupled to a memory circuit. An exemplary microcontroller includes a microprocessor and associated logic circuitry, which in combination with control logic circuits, timer logic, and an oscillator and clock circuit, generates the control and status signals that allow the microcontroller to control the operation of the IPG in accordance with a selected operating program and stimulation parameters.

The operating program and stimulation parameters are typically programmably stored within the memory circuitry by transmitting an appropriate modulated carrier signal through a receiving coil and charging and forward telemetry circuitry from an external programming unit, such as a handheld programmer (HHP) and/or a clinician programmer (CP), assisted as required through the use of a directional device. The handheld programmer may thus be considered to be in "telecommunicative" contact with the IPG. Similarly, the clinician programmer is considered to be in telecommunicative contact with the handheld programmer and, through the handheld programmer, with the IPG. The charging and forward telemetry circuitry demodulates the carrier signal it receives through the coil to recover the programming data (for example, the operating program and/or the stimulation parameters), which programming data is then stored within the memory or within other memory elements distributed throughout the IPG.

The microcontroller is further coupled to monitoring circuits via a bus. The monitoring circuits monitor the status of various nodes or other points throughout the IPG (e.g., power supply voltages, current values, temperature, the impedance of electrodes attached to the various electrodes, and the like). Informational data sensed through the monitoring circuit may be sent to a remote location external to the IPG (e.g., a non-implanted location) through back telemetry circuitry, including a transmission coil.

The electronic circuit board or hybrid (210) may also include power circuits. The power circuits may include protection circuitry that protects a replenishable power source from overcharging. Further, safeguarding features may be incorporated that help assure that the power source is operated in a safe mode upon approaching a charge depletion. Potentially endangering failure modes are reduced and/or prevented through appropriate logic control that is hard-wired into the device, or otherwise set in the device in such a way that a patient cannot override them.

The power source (220) may include a rechargeable battery, a primary battery, and/or a supercapacitor. Such a power source provides an unregulated voltage to power circuits described above. The power circuits, in turn, generate the various voltages, some of which are regulated and some of which are not, as needed by the various circuits located within the electronic circuit board or hybrid (210). The power circuits further selectively direct energy contained within the carrier signal, obtained through the charging and forward telemetry circuit, to the replenishable power source (220) during a charging mode of operation. In this manner, the replenishable power source (220) may be recharged.

According to one exemplary embodiment, the power source (220) includes a rechargeable battery, and more particularly, a rechargeable Lithium Ion battery. The power source (220) may be recharged inductively and transcutaneously, i.e., through the skin, from an external charging station. Further, an internal battery protection circuitry may be used for safety reasons, such as to prevent the battery from being overcharged and/or to only accept a charge from an authorized charging device. As described in further detail below, the power source (220) may be electrically coupled to the electronic circuit board or hybrid (210) to provide power to the electronic circuit board The flex connector (270) illustrated in FIG. 2 is configured to provide an electrical connection between the hybrid pins (230) of the electronic circuit board or hybrid (210) and the feedthru member (236). Consequently, the flex connector (270) may be made out of any number of electrically conductive materials including, but in no way limited to, platinum, copper, and the like. Additionally, the flex connector (270) may be manufactured using any number of appropriate means including, but in no way limited to, stamping, extruding, casting, and the like.

The electronic circuit board or hybrid (210), the power source (220), and the flex connector (270) are hermetically sealed within a case assembly that includes a case frame (240), side lids (250), and a feedthru member (236). The components of the case assembly may be repeatably and reliably formed using efficient methods of manufacture. Further, these components may be repeatably and reliably assembled, thereby increasing the yield rate of processes for forming IPG assemblies. Moreover, the illustrated configuration of the case assembly, which includes the case frame (240) and side lids (250) may allow for the use of less conductive materials (compared to a metal, e.g., titanium) like polyetheretherketone (PEEK) or ceramics that reduce or eliminate the creation of eddy currents during conductive charging of the power source (220). Consequently, faster charging rates of the power source (220) may be applied due to the reduced heating caused by eddy currents. An exemplary method of manufacturing the exemplary stimulator device (200) and the case assembly, as well as the specific details of each of the steps and the associated components will be discussed in more detail below with references to FIGS. 3 through 12.

Figure 3:
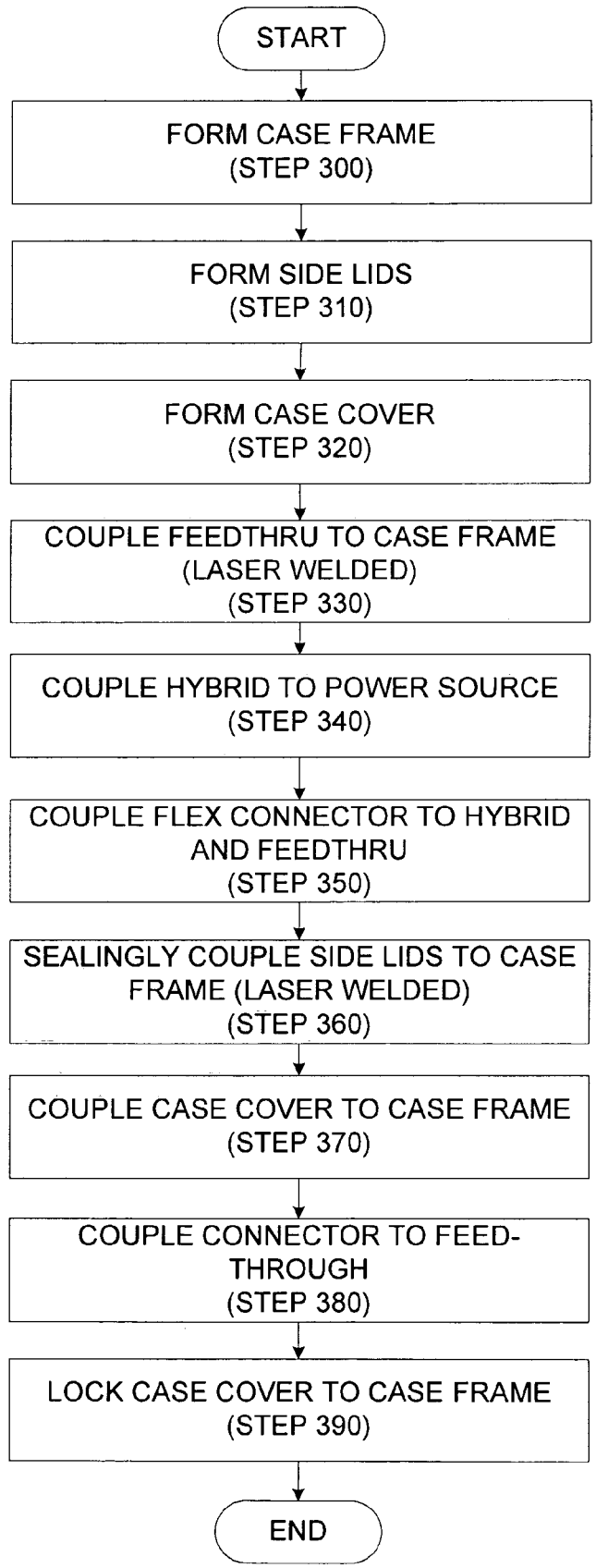
FIG. 3 is a flowchart illustrating a method of forming an implantable pulse generator, according to one exemplary embodiment.

FIG. 3 illustrates one exemplary method of forming an exemplary stimulator device. As illustrated in FIG. 3, the case frame is initially formed (step 300). Once the case frame is formed, the side lids are formed (step 310) in preparation for assembly. The case cover (also referred to as the connector block cover herein) is then formed (step 320) and the feedthru member is hermetically coupled to the case frame by such methods as laser welding (step 330). With the feedthru member hermetically coupled to the case frame, the circuit board or hybrid may be coupled to the power source (step 340) and the flex connector is coupled to both the circuit board or hybrid and the feedthru member (step 350). With the above-mentioned components properly coupled and placed within the case frame, the side lids may be sealingly coupled to the case frame (step 360) by such methods as laser welding to hermetically seal the exemplary case. Once hermetically sealed, the connector block cover may be coupled to the case frame (step 370) and a lead connector block may then be electrically coupled to the feedthru member (step 380) before the connector block cover is locked to the case frame (step 390). It also noted that in some embodiments, in accordance with the invention, wherein the case frame and side lids are made of a polymer/plastic, the case frame may be sealed but not necessarily hermetically sealed to gases, e.g., water vapor.

While FIG. 3 illustrates one exemplary method for forming an exemplary stimulator device, those of skill in the art will understand that the steps may be performed in several different orders and the present description is provided for ease of reference only. Further, not all steps need be performed. Further details of the exemplary method, along with detailed descriptions of the components involved will be given below with reference to FIGS. 3 through 12.

Figure 4:
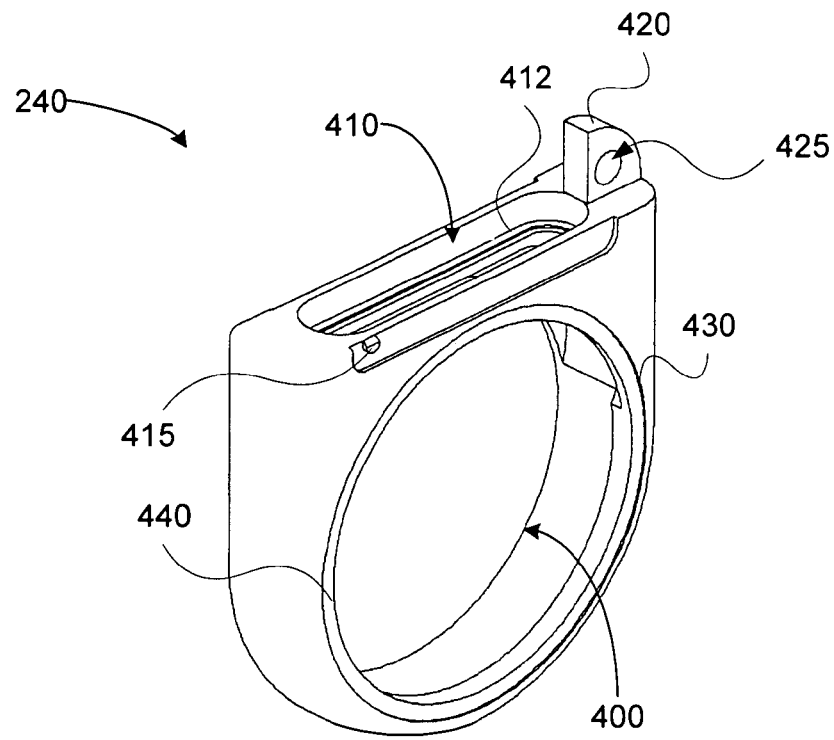
FIG. 4 illustrates a perspective view of an implantable pulse generator case, according to one exemplary embodiment.

As shown in FIG. 3, the present exemplary method begins by forming a case frame (step 300). An exemplary case frame is illustrated in FIG. 4. The case frame (240) illustrated in FIG. 4 is configured to have the electronic circuit board or hybrid (210; FIG. 2) and a power source (220; FIG. 2), in one embodiment, hermetically contained therein. In particular, the case frame (240), according to one exemplary embodiment, includes an outer portion and two opposing sides.

Figure 5:
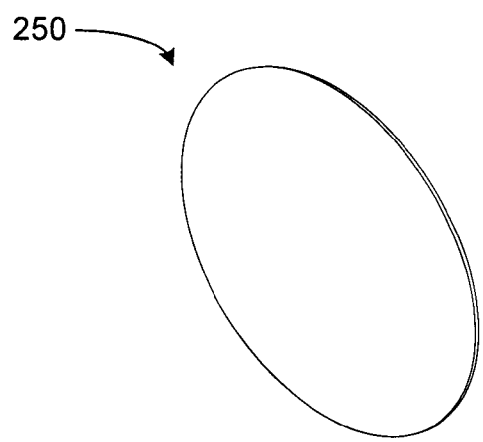
FIG. 5 illustrates a perspective view of a side lid, according to one exemplary embodiment.

As seen in FIG. 4, the case frame (240) includes a cavity (400), which is surrounded by the outer case frame portion and the cavity extends through the two opposing sides. The cavity (400) thus formed in the case frame (240) includes opposing perimeter portions (430) associated therewith that are formed on each of the opposing sides. These perimeter portions are generally planar. Further, according to one exemplary embodiment, the opposing sides are generally parallel to one another, such that the perimeter portions on each of the sides are also generally parallel. As illustrated in FIG. 4, a lid seat (440) is formed on each perimeter portion of the opposing sides to receive a side lid (250; FIG. 2 or FIG. 5). In some examples, the lid seats (440) may be recessed within the perimeter portion of the case frame (240). According to one exemplary embodiment, the lid seat (440) is configured to receive a side lid and seat it such that the outward surface of the side lid is flush with the perimeter portion (430) of the case frame (240). Such a seating of the side lid (250; FIG. 2) will facilitate coupling the side lid to the case frame (240) through improved laser welds.

The case frame (240) further includes a feedthru opening (410) defined therein. The feedthru opening (410), according to the present exemplary embodiment, is formed between the two opposing sides and extends through the outer portion and into the cavity (400). Accordingly, the feedthru opening (410) extends from the outer portion of the case frame (240) to the cavity (400). According to this exemplary embodiment, the feedthru opening (410) is configured to receive and properly seat a feedthru member (236; FIG. 2) therein.

According to one exemplary embodiment illustrated in FIG. 4, the feedthru opening (410) includes a seat lip (412) configured to interact with and properly seat a feedthru member (236; FIG. 2), as will be described in further detail below with reference to FIGS. 7 and 8.

Continuing with FIG. 4, the case frame (240) may also include a pair of locking protrusions (415) formed on a first side thereof and a pivot protrusion (420) having a pin orifice (425) formed therein on a second side thereof. According to one exemplary embodiment illustrated below, the locking protrusions (415) are configured to interact with and securely lock the connector block cover (260; FIG. 2) to the case frame (240).

Continuing with FIG. 4, the case frame (240) may be formed of any suitable materials. Suitable materials include, without limitation, titanium alloys including Ti 3.25 Al/4 Va and Ti 6 Al/4 Va, PEEK, ceramics, and any other suitable biocompatible metallic, non-metallic materials, or combinations thereof. The case frame (240) may also be formed by any suitable methods, such as by molding or machining. According to one exemplary embodiment, Titanium alloys are used to form the case frame (240) because they are less conductive than some other metallic materials. The case frame and side lids, in some embodiments, may be non-metallic, e.g., a ceramic or a polymer/plastic. The use of a less conductive alloy, such as a Titanium alloy or a non-metallic material such as PEEK or ceramics, may reduce the effects of eddy currents during charging of the power source (220; FIG. 2), which in turn may allow for an increased charge rate of the power source (220; FIG. 2).

Returning again to FIG. 3, the case frame (240; FIG. 2) can be formed (step 300), the side lids can be formed (step 310) in separate steps and the order of completion is not important. One exemplary side lid (250) is shown in FIG. 5. The side lids (250) correspond closely in shape to the perimeter portions (430; FIG. 4) and the lid seat portions (440; FIG. 4) on opposing sides associated with the cavity (400; FIG. 4) of the case frame (240; FIG. 2). Accordingly, the side lids (250) are configured to be coupled to the case frame (240) to seal each of the side portions. According to one exemplary embodiment, the side lids (250) are formed of such a thickness that they will have an outer surface flush with the outer surface of the perimeter portion (430) when seated in the lid seat (440).

The side lids (250) illustrated in FIG. 5 may be formed by any suitable method. Suitable methods include, without limitation, machining, and/or molding. The side lids may also be formed of any suitable biocompatible material, including, without limitation, titanium alloys, ceramics such as high-density alumina, polymers/plastics (e.g., PEEK), and/or any other weld-able or braze-able biocompatible material. According to exemplary embodiments, titanium or a non-metallic material such as a ceramic or PEEK may be used to form the side lid (250). By optionally using a non-metallic material to form the side lid (250), eddy current effect is reduced or eliminated in the side lid during a power source (220) recharging operation. The reduction or elimination of eddy current effects may allow for an increased charge rate for the power source, as discussed above. Additionally, even if the side lids are made of material affected by eddy currents, such as titanium, the thickness of the side lids (250) may be manipulated to reduce the eddy current effects generated during a recharging operation. Specifically, the side lids (250) may be made thinner to reduce eddy current effects.

Figure 6:
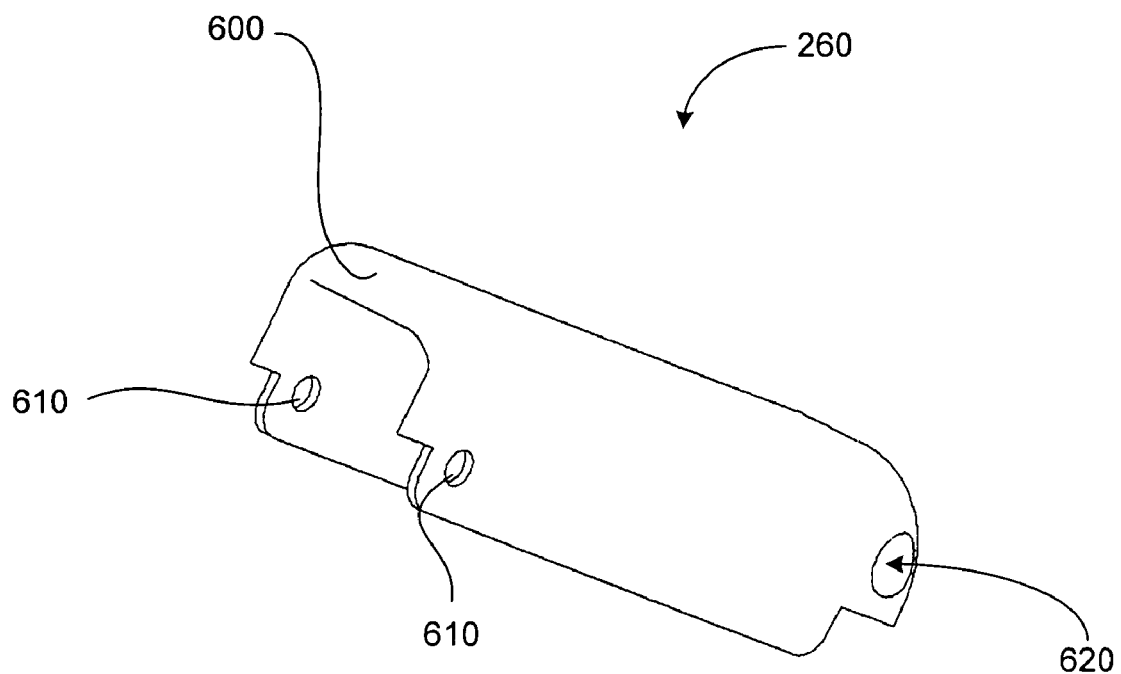
FIG. 6 illustrates a perspective view of a connector block cover, according to one exemplary embodiment.

Referring again to FIG. 3, the next exemplary step in forming an IPG is to form the connector block cover (step 320). An exemplary connector block cover (260) is shown in detail in FIG. 6. As illustrated in FIG. 6, the connector block cover (260) includes a top (600) and two spaced-apart lock-receiving orifices (610) formed in a first end thereof. Additionally, a pin orifice (620) may be formed in a second end of the connector block cover (260) as shown.

According to one exemplary embodiment, the lock receiving orifices (610) are formed in opposing side walls of the connector block cover (260). As shown, the lock receiving orifices (610) are shaped such that the connector block cover (260) may be coupled to the case frame (240; FIG. 4) by engagement with lock protrusions (415; FIG. 4) located on the opposite sides of frame (240). The lock receiving orifices (610) may be generally parallel to each other located on opposite sides of cover (260) walls. According to the present exemplary embodiment, the lock receiving orifices (610) are configured to lockingly interact with the locking protrusions (415; FIG. 4) of the case frame (240; FIG. 4).

As illustrated in FIG. 6, the connector block cover (260) also includes a pin orifice (620) formed in a first end of the connector block cover. According to the present exemplary embodiment, the pin orifice (620) is configured to be concentrically aligned with the pin orifice (425; FIG. 4) of the pivot protrusion (420; FIG. 4) during assembly, thereby forming a lumen configured to allow the insertion of a hinge pin (not shown).

The connector block cover (260) illustrated in FIG. 6 may be made of any suitable material including, without limitation, titanium alloys such as Ti 3.25 Al/4 Va and Ti 6 Al/4 Va, and any other suitable biocompatible metallic or non-metallic materials. During operation, the connector block cover (260) helps ensure that a lead connector block (1000; FIG. 10) coupled to the exemplary stimulator device (200) maintains electrical coupling, as will be described in further detail below.

Again referring to the flowchart shown in FIG. 3, the next step is to couple the feedthru member to the case frame (step 330). An exemplary feedthru member (236) is shown in more detail in FIG. 7. The feedthru member (236) provides the electrical connection between the circuit board (210; FIG. 2) and the lead connector block (1000; FIG. 10) via a number of feedthru pins (770) that extend through both sides of the feedthru member. According to one exemplary embodiment, the feedthru pins (770) are made of a conductive material such as platinum and are surrounded by an insulating material (775) such as glass to electrically isolate each feedthru pin. When assembled, the feedthru pins (770) electrically couple the flex connector (270) and a lead connector.

Figure 7:
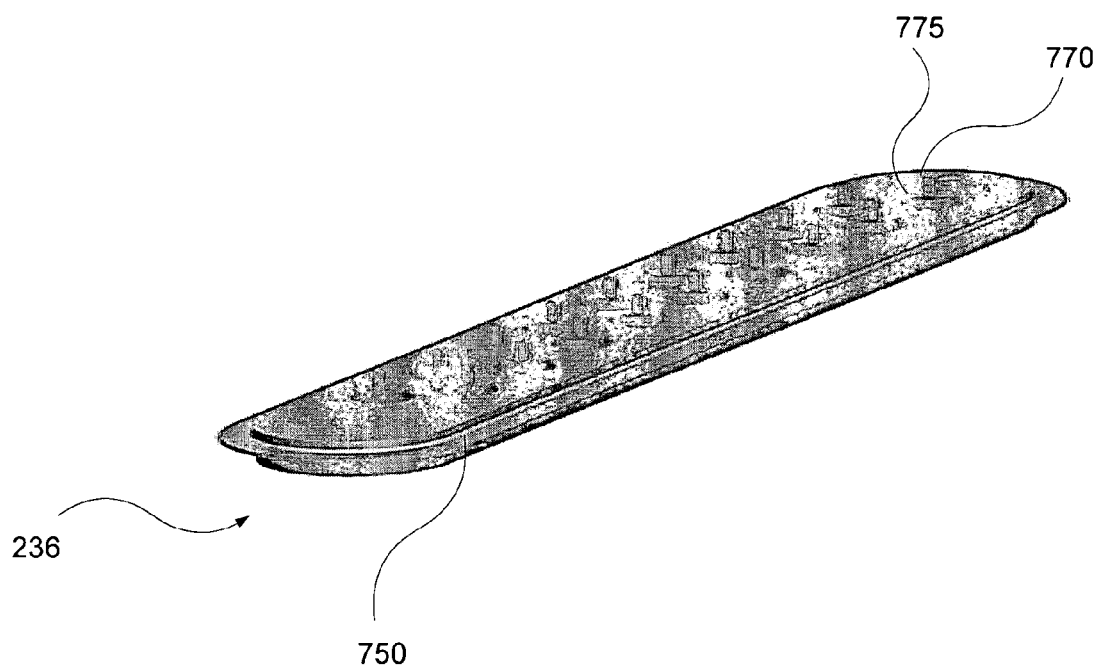
FIG. 7 illustrates a feedthru member, according to one exemplary embodiment.
Figure 8:
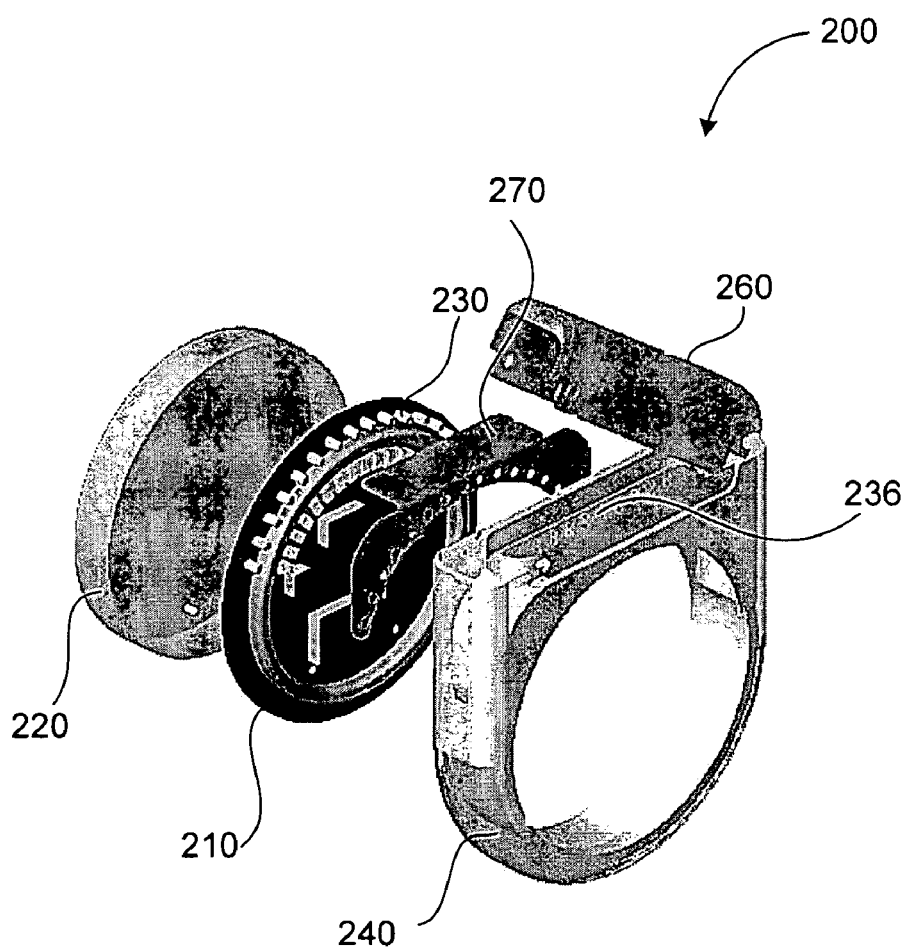
FIG. 8 illustrates an exploded view of an exemplary stimulator device assembly, according to one exemplary embodiment.

The feedthru member (236) may be secured in the feedthru opening (410; FIG. 4) as illustrated in FIG. 8. As shown, the feedthru member (236) includes a number of feedthru pins (770) that provide the electrical connection between the flex connector (270) sealed within the case frame (240) and a lead connector (not shown). According to one exemplary embodiment, the feedthru member (236) includes a circumferential flange (750; FIG. 7) that is configured to seat on the seat lip (412; FIG. 4) in the feedthru opening (410; FIG. 4) and be sealingly coupled to the case frame (240). The feedthru member (236) may be sealingly coupled to the feedthru opening (410) of the case frame (240) by an adhesive, welding, and the like. According to one exemplary embodiment, feedthru member (236) is laser welded to the seat lip (412; FIG. 4) of the case frame (240). As illustrated in FIGS. 4 and 7, the present exemplary configuration enables superior welding when compared to traditional IPG cases due to the interaction between the circumferential flange (750; FIG. 7) and the seat lip (412; FIG. 4). More specifically, the present exemplary configuration provides for improved hermetic joining of the feedthru member (236) to the case frame (240) by providing joinable material beneath the circumferential flange (750; FIG. 7).

Returning again to FIG. 3, the exemplary formation method continues by coupling the electronic circuit board or hybrid (210; FIG. 2) to the power source (step 340). According to one exemplary embodiment, the power source (220) is coupled to the electronic circuit board or hybrid (210) by soldering or by the use of conductive epoxy. Any other suitable process for coupling a desired power source (220) to the electronic circuit board or hybrid (210) may also be used.

With the desired power source (220) coupled to the electronic circuit board or hybrid (210), the flex connector (270) may then be coupled to both the electronic circuit board or hybrid (210) and the feedthru member (236). According to one exemplary embodiment, the flex connector (270) is coupled to both the electronic circuit board or hybrid (210) and the feedthru member (236) by first electrically coupling the flex connector to the hybrid pins (230) of the electronic circuit board or hybrid, and then inserting the assembly into the cavity (400) of the case frame (240). As the coupled flex connector (270), electronic circuit board or hybrid (210), and power source (220) are correctly inserted into the cavity (400) of the case frame (240), the flex connector (270) is placed in contact with the feedthru pins (770; FIG. 7) of the feedthru member (236).

Once the flex connector (270) is electrically coupled to both the electronic circuit board or hybrid (210) and the feedthru member (236), the side lids (250) may be sealingly coupled to the case frame (step 360; FIG. 3), forming a hermetic seal. According to one exemplary embodiment, the side lids (250) are first seated in the lid seats (440; FIG. 4) of the case frame (240). Once seated, the side lids (250) are laser welded to the case frame (240) thereby hermetically sealing the case. As previously discussed, the perimeter portions (430) of the cavity (400; FIG. 4) on each side of the case frame (240) are generally planar, according to the present exemplary embodiment. Such a planar configuration may allow for the rapid and reliable assembly of the exemplary stimulator device (200). In particular, the generally planar interface between the side lids (250) and the perimeter portions (430) of the case frame (240) may allow for a constant distance between a laser welding head, and the case frame and side lids. As a result, weld quality is increased and the side lids may be reliably and rapidly coupled to the case frame. Alternatively, the side lids (250) may be sealingly coupled to the case frame by any other suitable methods.

Figure 9:
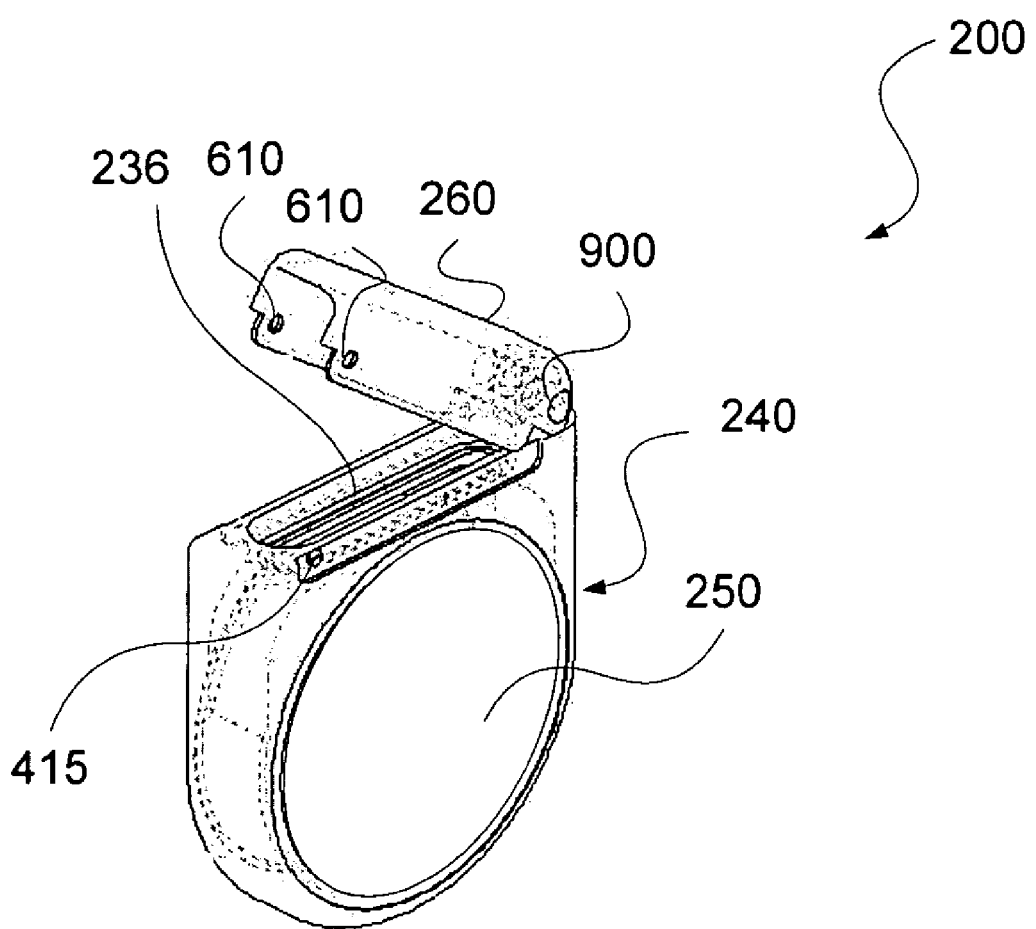
FIG. 9 is a perspective view illustrating an assembled stimulator device (excluding the lead connector block), according to one exemplary embodiment.

After the side lids (250) are coupled to the case frame (240), a connector block cover (260) may be coupled to the case frame (step 370). As illustrated in the exemplary embodiment of FIG. 9, the connector block cover (260) may be pivotably coupled to the case frame (240) by concentrically aligning the pin orifice (425; FIG. 4) of the case frame (240) and the pin orifice (620; FIG. 6) of the connector block cover (260). Once the pin orifices are concentrically aligned, a hinge pin (900; FIG. 9) may be passed therethrough. As illustrated in FIG. 9, the insertion of the hinge pin (900) allows the connector block cover (260) to pivot relative to the case frame (240) on one end. As illustrated in FIG. 10, the connector block cover (260) may be pivoted about the hinge pin (900) to expose the feedthru member (236) for reception of a lead connector block (1000).

Figure 11:
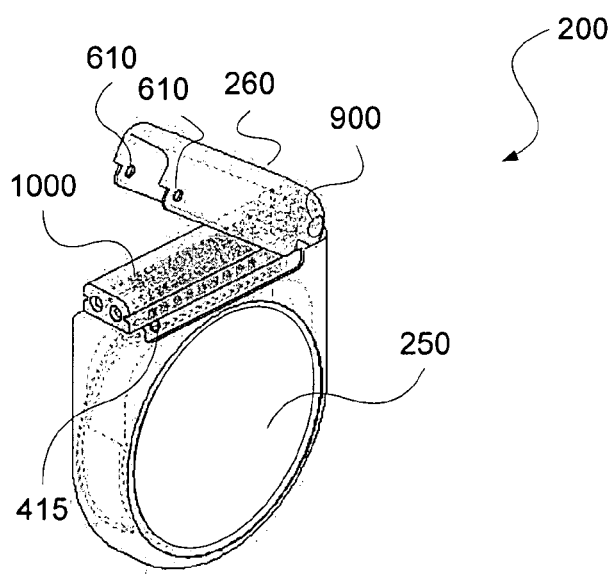
FIG. 11 is a perspective view of a lead connector block inserted into an assembled stimulator device, according to one exemplary embodiment.
Figure 12:
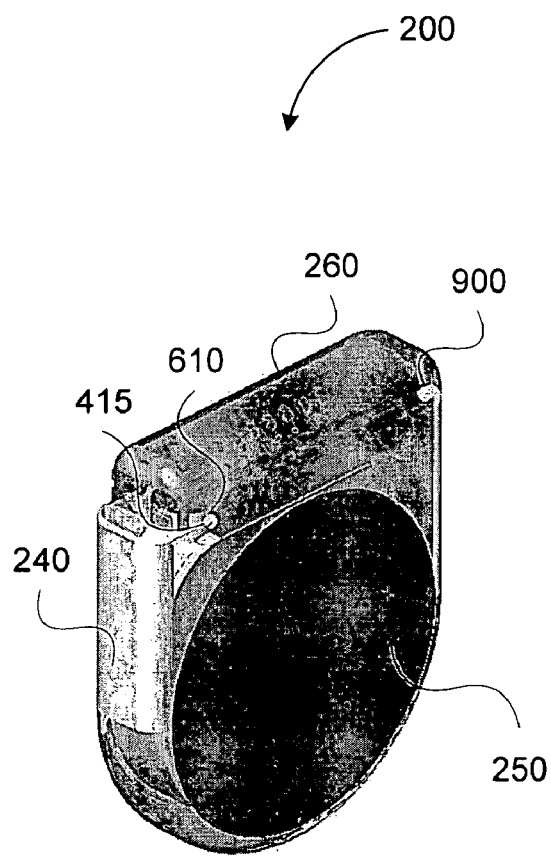
FIG. 12 is a perspective view of an assembled stimulator device with the connector block cover in a locked position, according to one exemplary embodiment.

Again referring to FIG. 3, after the side lids are coupled to the case frame, a lead connector block is coupled to the feedthru member (step 380). According to the exemplary embodiment illustrated in FIG. 10, a lead connector block (1000) may be seated in the case frame in proximity to the connector block cover (260). When completely inserted, the lead connector block may be seated in the case frame (240) coupled to the feedthru member (236) as shown in FIG. 11. When the lead connector block (1000) is properly seated in the case frame (240), the lead connector block forms an electrical connection with the conductive pins of the feedthru member (236), and consequently, the electronic circuit board or hybrid (210). As previously introduced, a suitable lead connector is described more fully in commonly assigned U.S. patent application entitled "Connector for Use in An Implantable Stimulator Device", referenced above. Additionally, any other suitable lead connector may also be used.

Returning again to FIG. 3, once the lead connector block has been electrically coupled to the feedthru member (step 380), the connector block cover may be locked to the case frame (step 390). According to one exemplary embodiment illustrated in FIG. 12, the connector block cover (260) is secured to the case frame (step 390), thereby securing the lead connector block inside the resulting case.

More particularly, according to one exemplary embodiment, the connector block cover (260) is configured to interact with the case frame (240) to lock the lead connector block between the case frame and the connector block cover. According to the exemplary embodiment illustrated in FIG. 12, locking the connector block cover (260) to the case frame (240) includes pivoting the connector block cover (260) about the hinge pin (900) until the lock receiving orifices (610) formed in the connector block cover overlap and engage the lock protrusions (415) formed in the case frame (245). As the connector block cover (245) is closed and secured to the case frame (245), the connector block cover (260) and case frame (245) exert compressive forces on the lead connector block (1000). The compressive forces, produced by the connector block cover (260) and the case frame (245), are then transferred to the lead connector block (1000), securing the lead connector block to the feedthru member (236). While the present stimulator device (200; FIG. 1) is described in the context of using a locking protrusion and lock receiving orifice combination, those of skill in the art will appreciate that any type of locking may be used to secure the connector block cover (260) to the case frame (240) including, but in no way limited to, a small set screw.

Figure 13:
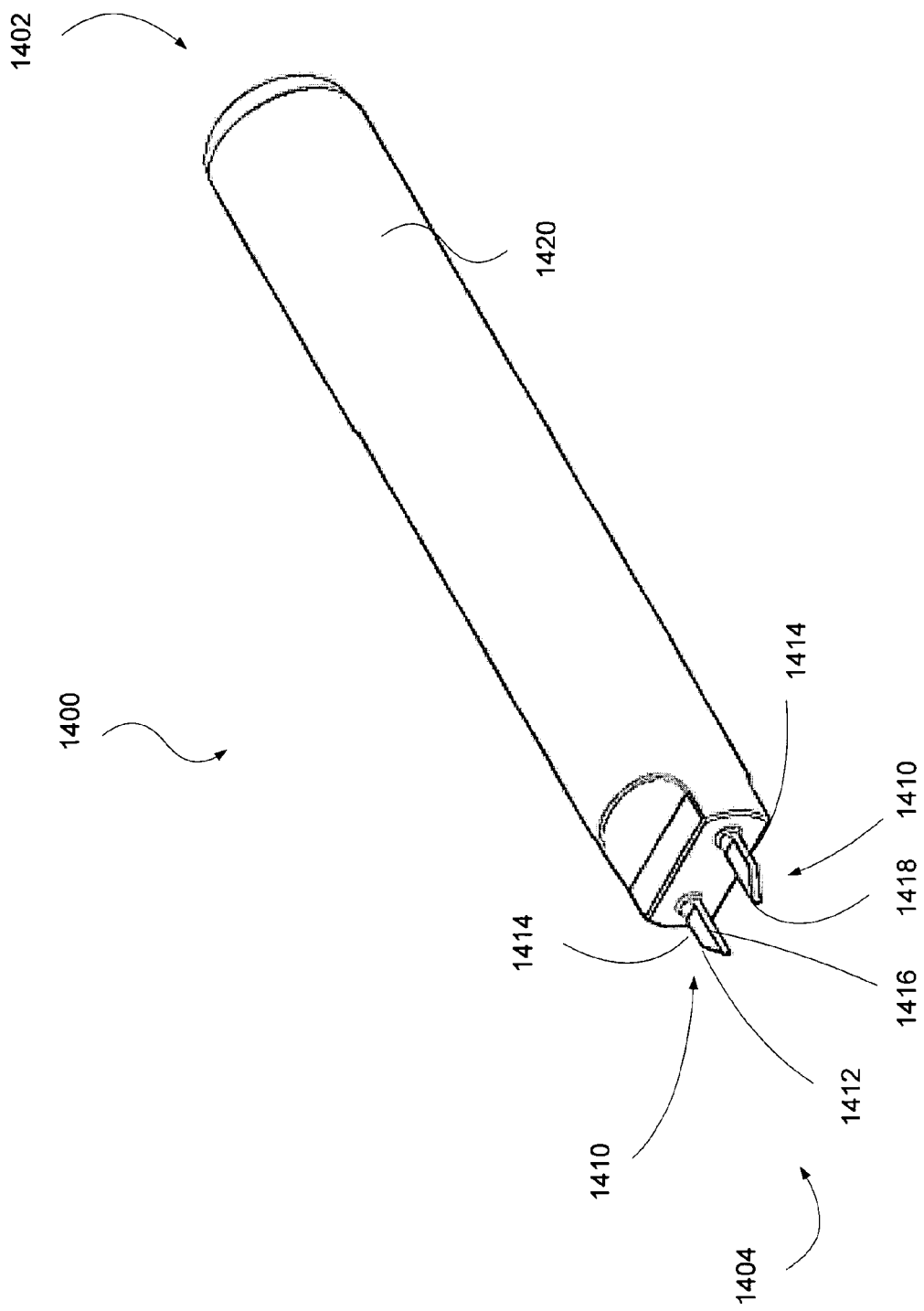
FIG. 13 is a perspective view of a prying tool configured to unlock the connector block cover, according to one exemplary embodiment.

Under some circumstances, it may be desired to open or unlock the connector block cover (260) relative to the case frame (240) after it has been secured or locked. For example, if a lead or lead extension (not shown) is not inserted fully into the lead connector block (1000), the lead or lead extension may need to be re-inserted. Hence, the connector block cover (260) must be unlocked. To unlock the connector block cover (260), the walls of the connector block cover (260) having the lock receiving orifice (610) formed therein may be spread apart to eliminate the interference between the lock receiving orifices (610) and the locking protrusions (415). According to one exemplary embodiment, a prying tool (1400) illustrated in FIG. 13 may be used to spread the walls of the connector block cover (260) sufficiently to unlock the connector block cover. As illustrated in FIG. 13, the prying tool (1400) includes a body portion (1420) having a first end (1402) and a second end (1404). The body portion (1420) is configured to serve as a handle for the operation of the prying tool (1400).

Additionally, as illustrated in FIG. 13, the second end (1404) of the prying tool (1400) includes a number of prying prongs (1410) projecting therefrom. According to the illustrated embodiment, the prying prongs each include an external cover edge (1414) and an internal lock edge (1416) formed substantially parallel with the longitudinal axis of the prying tool (1400). The proximal end of each prying prong terminates with an inclined face (1412) forming a point (1418) with the lock edge (1416) as shown.

Figure 14A:
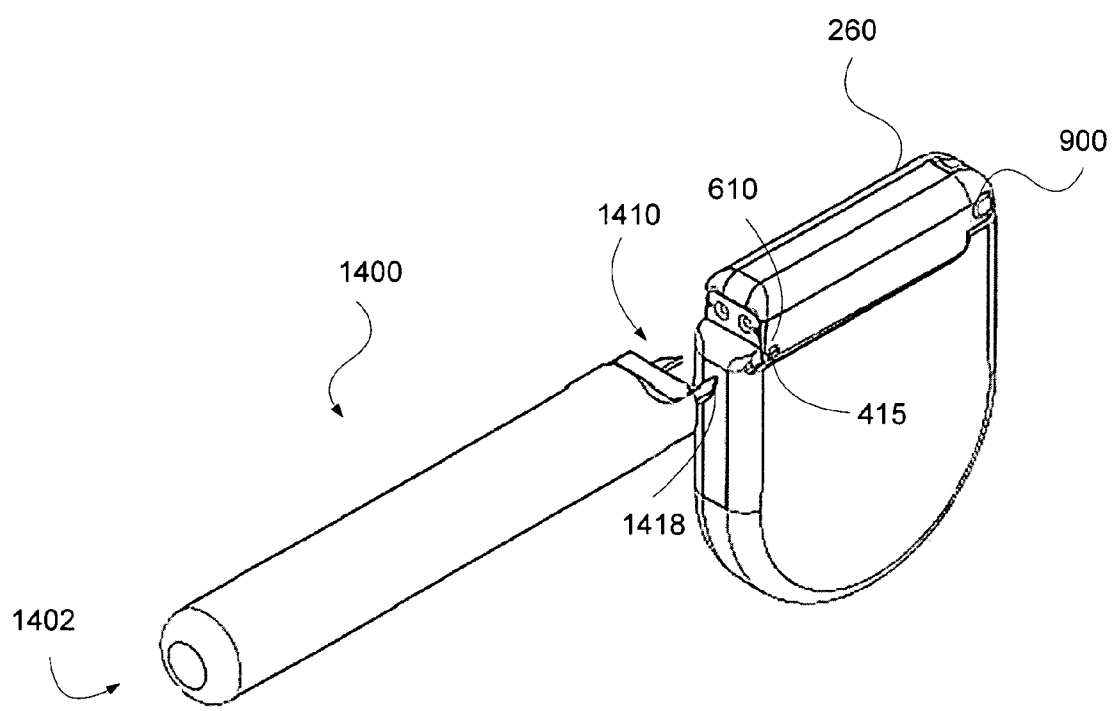
FIGS. 14A through 14C illustrate the unlocking of a connector block cover with the prying tool, according to one exemplary embodiment.
Figure 14B:
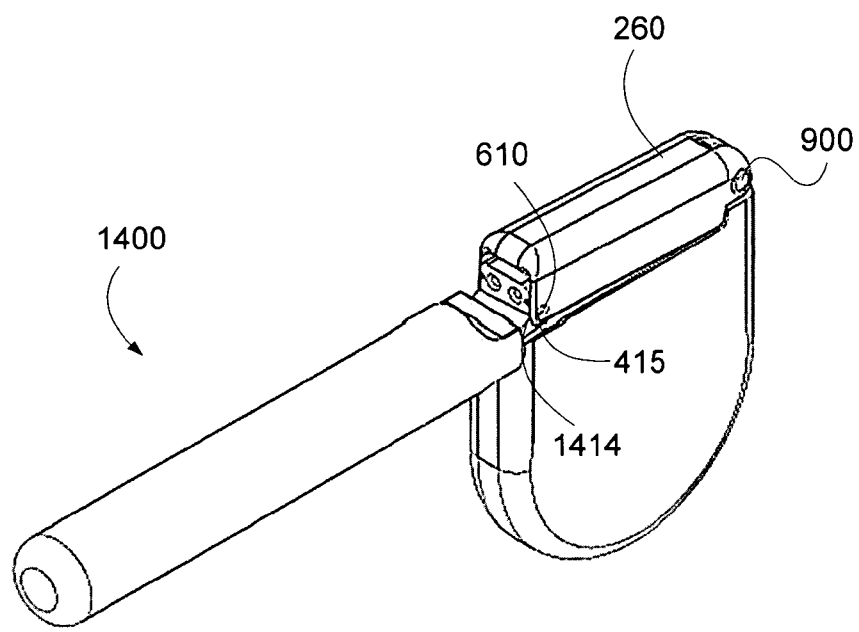
Figure 14C:
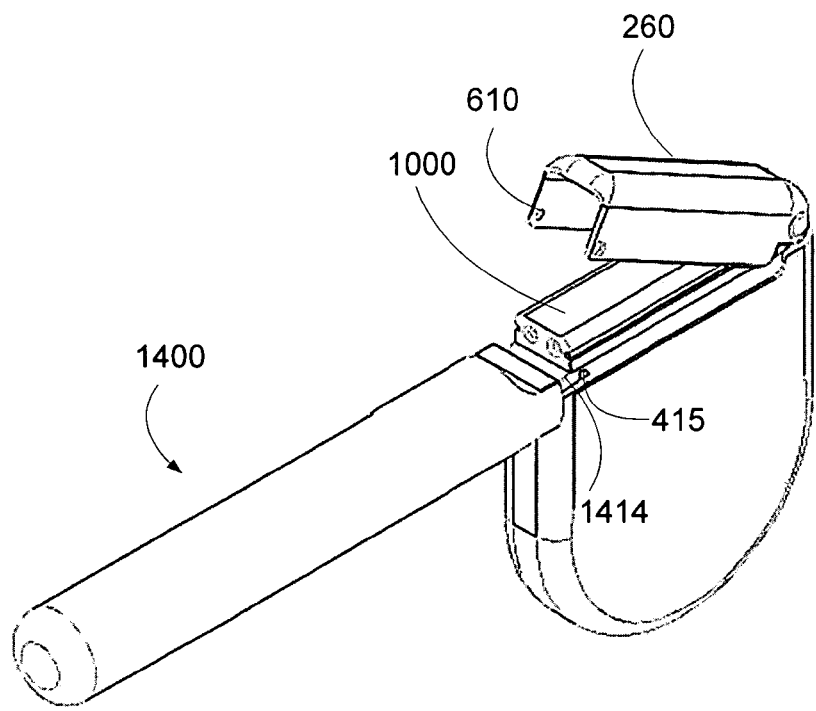

FIGS. 14A through 14C illustrate an exemplary method for opening or unlocking a connector block cover (260) relative to the case frame (245) after it has been secured, using the present prying tool (1400). As illustrated in FIG. 14A, one end of the prying tool (1400) having the prying prongs (1410) formed thereon is presented adjacent to the connector block cover (260) where the lock receiving orifices (610) engage the locking protrusions (415).

The prying prongs (1410) of the prying tool (1400) are then inserted between the connector block cover (260) and the case frame (245) as illustrated in FIG. 14B. According to the present exemplary embodiment, the point (1418) of each prying prong (1410) initiates the insertion and the lock edge (1416) of the prong then follows the profile of the case frame (245). As the lock edge (1416) of each prying prong (1410) follows the profile of the case frame (245), the inclined faces (1412) force the walls of the connector block cover (260) away from the case frame (245). As the walls of the connector block cover (260) are forced away from the case frame (245), the lock receiving orifices (610) are also forced away from the locking protrusions (415), thereby eliminating the interference between the orifices and the protrusions.

As illustrated in FIG. 14C, with the interference between the lock receiving orifice (610) and the locking protrusions (415) eliminated, the connector block cover (260) is unlocked and may be opened. When the connector block cover (260) is thereby opened, the compressive forces to the lead connector block (1000) are eliminated. As these compressive forces are removed, the lead connector block (1000) substantially returns to its uncompressed shape.

In conclusion, a case assembly has been discussed herein that may be used to hermetically seal an implantable pulse generator. The case assembly generally includes a case frame with a cavity defined therein and extending between opposing sides. The cavity is configured to have an electronic circuit board or hybrid and a power source contained therein. The case assembly also includes side lids configured to be coupled to the case frame to thereby seal each of the opposing sides. The configuration of the present side lids and feedthru member described herein allows for the rapid and reliable formation of an implantable pulse generator. The weld orientations and material placement further aid in providing reliable welds. Further, the case frame, the side lids, and the case frame can be precisely machined with very high precision and high tolerances on machine tool centers. Moreover, the present configuration allows for greater flexibility in the geometrical and material properties of the frame and side lids, thereby allowing for the design of components that reduce undesired effects, such as eddy currents during power supply recharging.

The preceding description has been presented only to illustrate and describe the present method and apparatus. It is not intended to be exhaustive or to limit the disclosure to any precise form disclosed. Many modifications and variations are possible in light of the above teaching. It is intended that the scope of the disclosure be defined by the following claims.

What is claimed is:

1. A case assembly, comprising:
   a case frame having a perimeter portion defining a cavity extending completely through said case frame and configured to contain at least one electronic component, said perimeter portion comprising a first outer surface and a second outer surface disposed opposite said first outer surface;
   a feedthru opening defined in said case frame;
   a feedthru member configured to fit within said feedthru opening, sealingly couple to said case frame, and electrically couple to said at least one electronic component;
   a first recessed lid seat disposed in said first outer surface of said perimeter portion;
   a second recessed lid seat disposed in said second outer surface of said perimeter portion;
   a first side lid configured to fit within said first recessed lid seat and sealingly couple to said case frame; and
   a second side lid configured to fit within said second recessed lid seat and sealingly couple to said case frame.

2. The assembly of claim 1, wherein:
   said first and second outer surfaces are substantially planar.

3. The assembly of claim 1, wherein said feedthru member comprises:
   a body including a circumferential flange; and
   a plurality of electrically conductive pins extending through said body.

4. The assembly of claim 3, wherein said feedthru opening comprises:
   a lumen extending from an outer surface of said case frame to said cavity; and
   a seat lip disposed within said lumen for seating a feedthru member.

5. The assembly of claim 1, wherein said case frame comprises at least one of a titanium alloy, ceramic and plastic.

6. The assembly of claim 5, wherein said case frame is a titanium alloy comprised of Ti 6 Al/4V.

7. The assembly of claim 1, wherein said at least one side lid comprises one of a braze-able biocompatible material or a weldable biocompatible material.

8. The assembly of claim 1, wherein said at least one side lid comprises one of a titanium alloy, a ceramic, or a polyetheretherketone (PEEK).

9. The assembly of claim 8, wherein said ceramic material comprises high density alumina.

10. The assembly of claim 1, further comprising:
    a removable lead connector block, wherein the lead connector block is configured to be seated into a portion of the case frame;
    a connector block cover that is movably connected to the case frame, and which connector block cover has an unlocked position and a locked position, wherein in the locked position the connector block cover secures the lead connector block to the case frame.

11. An implantable medical device comprising:
    a power source;
    pulse generating electronics coupled to said power source;
    a case assembly including:
      a case frame having a perimeter portion defining a cavity extending completely through said case frame and configured to contain said pulse generating electronics and said power source, said perimeter portion comprising a first outer surface and a second outer surface disposed opposite said first outer surface;
      a feedthru opening defined in said case frame;
      a feedthru member configured to fit within said feedthru opening, sealingly couple to said case frame, and electrically couple to said pulse generating electronics;
      a first recessed lid seat disposed in said first outer surface of said perimeter portion;
      a second recessed lid seat disposed in said second outer surface of said perimeter portion;
      a first side lid configured to fit within said first recessed lid seat and sealingly couple to said case frame; and
      a second side lid configured to fit within said second recessed lid seat and sealingly couple to said case frame.

12. The device of claim 11, further comprising:
    a removable lead connector block, wherein the lead connector block is configured to be seated into a portion of the case frame.

13. The device of claim 12, further comprising:
    a connector block cover that is movably connected to the case frame, which connector block cover has an unlocked position and a locked position, wherein in the locked position, the connector block cover secures the lead connector block to the case frame.

14. The device of claim 11, wherein said power source comprises a replenishable power source.

15. The device of claim 11, wherein said first and second surfaces are substantially planar.

16. The assembly of claim 1, wherein said first and second side lids each have a thickness configured to minimize one or more effects of eddy current.

17. The assembly of claim 1, wherein said case frame and said side lids are made of a machined material.

18. The device of claim 11, wherein said first and second side lids each have a thickness configured to minimize one or more effects of eddy current.

19. The device of claim 11, wherein said case frame and said side lids are made of a machined material.

* * * * *